(12) United States Patent
Chua et al.

(10) Patent No.: US 7,816,524 B2
(45) Date of Patent: Oct. 19, 2010

(54) METHODS OF PREPARING QUINOLONE ANALOGS

(75) Inventors: Peter C. Chua, San Diego, CA (US); Johnny Y. Nagasawa, San Diego, CA (US); Michael Schwaebe, San Diego, CA (US); Fabrice Pierre, La Jolla, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 381 days.

(21) Appl. No.: 11/499,076

(22) Filed: Aug. 4, 2006

(65) Prior Publication Data

US 2007/0032652 A1    Feb. 8, 2007

Related U.S. Application Data

(60) Provisional application No. 60/705,966, filed on Aug. 5, 2005.

(51) Int. Cl.
- *C07D 491/22* (2006.01)
- *C07D 471/22* (2006.01)
- *C07D 471/14* (2006.01)
- *C07D 513/22* (2006.01)
- *C07D 498/22* (2006.01)
- *A61P 35/00* (2006.01)

(52) U.S. Cl. .................... 544/247; 546/64; 546/81; 546/48; 546/65

(58) Field of Classification Search ............... 544/115, 544/247, 343; 546/64, 62, 94, 48, 82, 65, 546/81

See application file for complete search history.

(56) References Cited

U.S. PATENT DOCUMENTS 5,646,163 A    7/1997  Demuth et al.
6,960,585 B2 *  11/2005  Beaulieu et al. ............ 514/248

FOREIGN PATENT DOCUMENTS

WO    WO-2006/034113    3/2006

OTHER PUBLICATIONS

Nosova et al., Russian Chemical Bulletin (2005) 54(3):733-737.
International Search Report for PCT/US2006/030409, mailed on Oct. 30, 2006, 4 pages.
Written Opinion of the International Searching Authority for PCT/US2006/030409, mailed on Oct. 30, 2006, 5 pages.
Abbotto et al., J. Org. Chem. (2002) 16:5753-5772.
Satchell and Satchell, Chem. Rev. (1969) 69:251-278.
Vaickus, Crit. Rev. in Oncol./Hemotol. (1991) 11:267-297.

\* cited by examiner

*Primary Examiner*—James O Wilson
*Assistant Examiner*—Cecilia M Jaisle
(74) *Attorney, Agent, or Firm*—Cooley LLP

(57) ABSTRACT

Compounds having formula 1

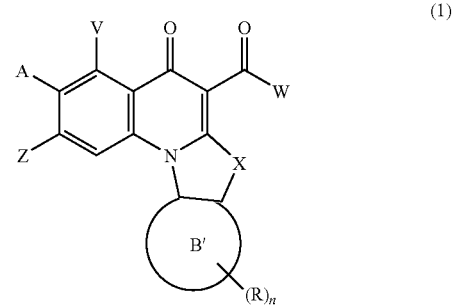

(1)

are produced by contacting a compound having formula (6A) with a compound having formula (7), or tautomers thereof, in the presence of a non-nucleophilic base,

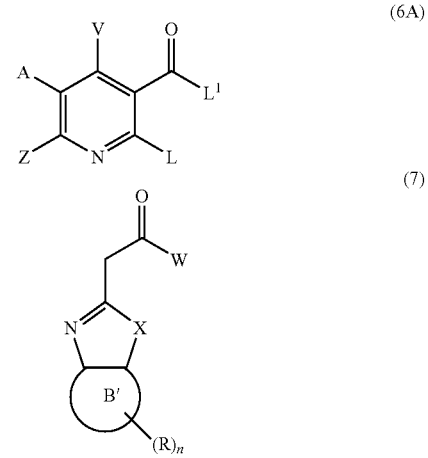

wherein V, A, Z, L, $L^1$, W, X, B', R and N are as defined herein.

22 Claims, No Drawings

METHODS OF PREPARING QUINOLONE ANALOGS

CROSS REFERENCE TO RELATED APPLICATIONS

This application claims the benefit of U.S. provisional patent application Ser. No. 60/705,966, filed Aug. 5, 2005, which is hereby incorporated by reference in its entirety.

SUMMARY OF THE INVENTION

The present invention relates to methods of preparing quinolone analogs. The compounds prepared according to the methods of the present invention may exhibit one or more of the following activities: inhibit cell proliferation, induce cell apoptosis and stabilize a quadruplex structure.

In one aspect, the present invention provides a method for preparing a compound having formula 1:

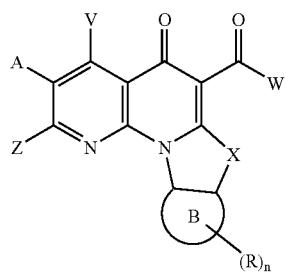

(1)

and pharmaceutically acceptable salts, esters and prodrugs thereof, wherein:

A, V, and Z are independently H, halo, cyano, $R^2$, $CH_2R^2$, $SR^2$, $OR^2$ or $NR^1R^2$; or wherein A and Z, or V and Z may form a carbocyclic ring, heterocyclic ring, aryl or heteroaryl, each of which may be optionally substituted and/or fused with a cyclic ring;

W is $NR^1R^2$ or $OR^6$ wherein $R^6$ is a $C_{1-10}$ alkyl;

X is O, S, $CR^1$ or $NR^1$;

each $R^1$ is H or a $C_{1-6}$ alkyl;

each $R^2$ is H, or a $C_{1-10}$ alkyl or $C_{2-10}$ alkenyl each optionally substituted with a halogen, one or more non-adjacent heteroatoms, a carbocyclic ring, a heterocyclic ring, an aryl or heteroaryl, wherein each ring is optionally substituted;

R is a substituent at any position on B; and is H, $OR^2$, amino, alkoxy, amido, halogen, cyano or an inorganic substituent; or R is $C_{1-6}$ alkyl, $C_{2-6}$ alkenyl, —CONHR', each optionally substituted by one or more non-adjacent heteroatoms; or two adjacent R are linked to obtain a 5-6 membered optionally substituted carbocyclic or heterocyclic ring, optionally fused to an additional optionally substituted carbocyclic or heterocyclic ring;

B is an optionally substituted ring, which may be aromatic or nonaromatic, and may be monocyclic or fused with a single or multiple ring, wherein said single or multiple ring may optionally contain one or more heteroatoms;

n is 1-6;

or a compound having formula (2A) or (4A):

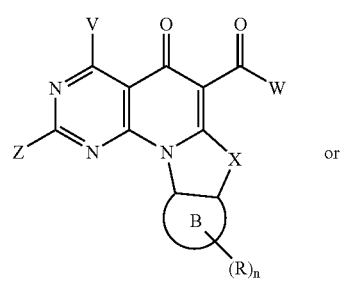

(2A)

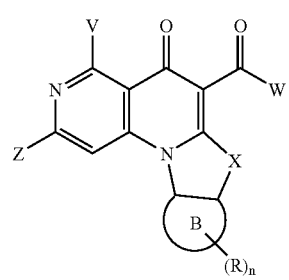

(4A)

wherein n, V, Z, X, W, B and R are as defined in formula (1), comprising:

contacting a compound having formula (6A), (6B) or (6C)

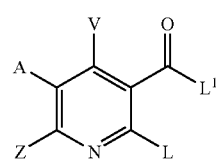

(6A)

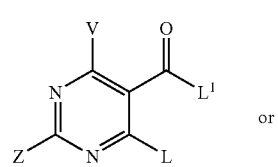

(6B)

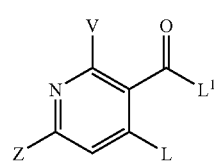

(6C)

wherein each L and $L^1$ is a leaving group; and A, V, and Z are as defined in formula (1);

with a compound having formula (7) and tautomers thereof

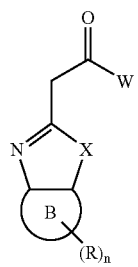

(7)

wherein n, X, B and R are as defined in formula (1); and
W is $OR^6$ wherein $R^6$ is a $C_{1-10}$ alkyl; or W is $NR^1R^2$,
wherein $R^1$ and $R^2$ are as defined in formula (1);
wherein said compound having formula (6A), (6B) or (6C)
is contacted with said compound having formula (7) and
tautomers thereof in the presence of a base to produce a
compound having formula (1), and optionally hydrolyzing said compound of formula (1).

In the above method, the compound having formula (6A),
(6B) or (6C) may be contacted with a compound of formula
(7) or tautomers thereof in the presence of a base and coordinating atom, such as the coordinating metal of a Lewis acid.

In particular examples, the base is a non-nucleophilic base
having a pKa of less than 20. Various bases known in the art
may be used to practice the methods of the invention, including but not limited to triethylamine (TEA), diisopropyl ethyl
amine (DIEA), iazabicycloundecene (DBU), cesium carbonate, 1,8-Bis(dimethylamino)naphthalene (Proton sponge)
and dimethylamino pyridine (DMAP).

Suitable Lewis acids for use in practicing the methods of
the invention may be selected by conducting a test reaction,
and observing the amount of reaction product produced, as
described hereafter. In one embodiment, the Lewis acid has
formula $ML_n$, wherein L is a halogen atom or an organic
radical, n is 3-5, and M is a group II metal, such as $MgCl_2$.
Other M groups include but are not limited to group III
elemental atom (e.g., B), a group IV elemental atom, As, Sb,
V or Fe.

In the above method, the compound having formula (1),
(2A) or (4A) wherein W is $OR^6$ and $R^6$ is a $C_{1-6}$ alkyl, may
further be contacted with an amine of the formula $HNR^1-(CR^1_2)_n-NR^3R^4$ (3)

wherein $R^1$ and $R^3$ are independently H or $C_{1-6}$ alkyl;
n is 1-6; and
$R^4$ is H, a $C_{1-10}$ alkyl or $C_{2-10}$ alkenyl optionally containing
one or more non-adjacent heteroatoms selected from N,
O and S, and optionally substituted with a carbocyclic or
heterocyclic ring; or $R^3$ and $R^4$ together with N may
form an optionally substituted ring containing one or
more N, O or S.

In the above formula (3), $R^3$ and $R^4$ together with N may
form an optionally substituted piperidine, pyrrolidine, piperazine, morpholine, thiomorpholine, imidazole, or aminothiadiazole.

In the above method, the compound having formula (1),
(2A) or (4A) wherein W is $OR^6$ and $R^6$ is a $C_{1-6}$ alkyl, may
further be contacted with an amine of the formula $HNR^1R^2$,
provided said amine is not $NH_3$. In the amine $HNR^1R^2$, the $R^1$
substituent may be H, and $R^2$ is a $C_{1-10}$ alkyl optionally
substituted with a heteroatom, a $C_{3-6}$ cycloalkyl, aryl or a 5-14
membered heterocyclic ring containing one or more N, O or
S; or $R^1$ and $R^2$ together with N may form an optionally
substituted heterocyclic ring containing one or more N, O or
S. In one example, $R^2$ is a $C_{1-10}$ alkyl substituted with morpholine, thiomorpholine, imidazole, aminothiadiazole, pyrrolidine, piperazine, pyridine or piperidine; or $R^1$ and $R^2$
together with N form piperidine, pyrrolidine, piperazine,
morpholine, thiomorpholine, imidazole, or aminothiadiazole.

In each of the above formula, B may be an optionally
substituted phenyl. Furthermore, each R in the above formula
may be H or halo. The X substituent in each of the above
formula may be $NR^1$ or S. In other examples, one of A and V
in each of the above formula is H or halo, such as a fluoro or
a chloro. In each of the above formula, each Z may be H, halo,
or $SR^2$ wherein $R^2$ is $C_{1-10}$ alkyl.

In the above formula (6A), (6B) or (6C), each L and $L^1$ is
suitable leaving group such as halo, sulfonate, sulfoxide,
sulfone, acyloxy, phosphonate, imidazole, benzotriazole, or
imide. Other leaving groups which may be suitable for use in
the methods of the invention include but are not limited to
tosylate, alkyl sulfonyl, carbonate, acetate, carbamate, trifluoroacetate, phosphate, methoxy or activated methoxy,
nitro, boron, or a substituted boron such as boronate esters.

In the above methods, a compound having formula (6A),
(6B) or (6C) may be contacted with a compound having
formula (7) to form a mixture, and further contacting the
mixture with a base. The mixture may be cooled to a temperature below room temperature prior to addition of base.
Alternatively, the base may be added to the mixture at room
temperature or at a temperature above room temperature. In
particular examples, the base is an amine, such as trialkylamine.

In one aspect, the methods of the present invention may be
used to prepare a compound having formula (2B), (4), (4B) or
(5A):

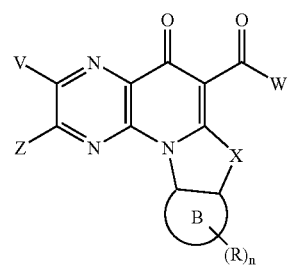

(2B)

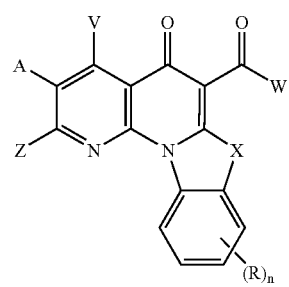

(4)

-continued

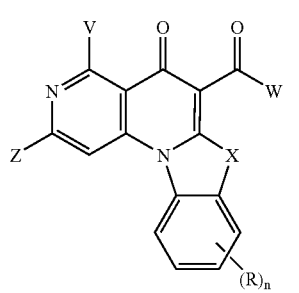

(4B)

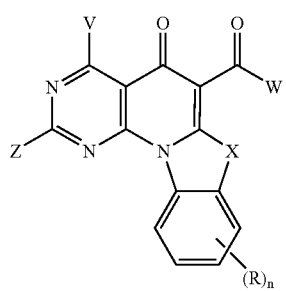

(5A)

wherein n, W, V, A, Z, X, B and R are as defined in formula (1)

In another aspect, the present invention provides methods for preparing a compound having formula (8)

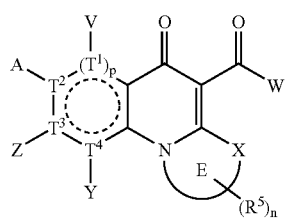

(8)

wherein V, A, Z, and Y when attached to C are independently H, halo, azido, $R^2$, $CH_2R^2$, $SR^2$, $OR^2$, $NR^1R^2$; or absent when attached to N;

$T^1$, $T^2$, $T^3$, and $T^4$ are independently C, N or S;

W is $NR^1R^2$ or $OR^6$, wherein $R^6$ is a $C_{1-10}$ alkyl;

X is O, S, $CR^1$ or $NR^1$;

E together with N and X form a ring, which may be fused with a single or multiple ring, wherein the single or multiple ring optionally contains one or more heteroatoms;

n is 1-6;

p is 0-1;

each $R^1$ is H or a $C_{1-6}$ alkyl;

each $R^2$ is H, or a $C_{1-10}$ alkyl or $C_{2-10}$ alkenyl each optionally substituted with a halogen, one or more non-adjacent heteroatoms, a carbocyclic ring, a heterocyclic ring, an aryl or heteroaryl, wherein each ring is optionally substituted;

$R^5$ is a substituent at any position on E; and is H, $OR^2$, amino, alkoxy, amido, halogen, cyano or an inorganic substituent; or R is $C_{1-6}$ alkyl, $C_{2-6}$ alkenyl, $—CONHR^1$, each optionally substituted by one or more non-adjacent heteroatoms; or two adjacent $R^5$ are linked to obtain a 5-6 membered optionally substituted carbocyclic or heterocyclic ring, optionally fused to an additional optionally substituted carbocyclic or heterocyclic ring;

comprising contacting a compound having a formula (9) with a compound having formula (10) and tautomers thereof:

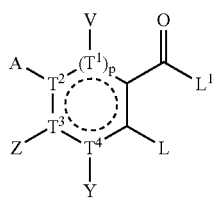

(9)

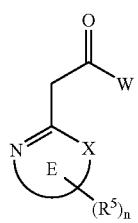

(10)

wherein n, V, A, Z, Y, $T^1$, $T^2$, $T^3$, $T^4$, X, W, E and $R^5$ are as defined in formula (8); and each L and $L^1$ is a leaving group.

In the above method, the compound having formula (9) may be contacted with a compound of formula (10) or tautomers thereof in the presence of a base and coordinating atom such as the coordinating metal of a Lewis acid. Various bases and Lewis acids, such as those previously described and which would be known to those skilled in the art, may be used.

In the above formula (8), each $T^1$, $T^2$, $T^3$ and $T^4$ may be C. In another embodiment, $T^1$ is N, and each $T^2$, $T^3$, and $T^4$ is C. In yet another embodiment, $T^2$ is N, and each $T^1$, $T^3$, and $T^4$ is C. In other embodiments, each $T^1$ and $T^3$ is N, and each $T^2$ and $T^4$ is C. In another embodiment, each $T^1$ and $T^4$ is N, and each $T^2$ and $T^3$ is C. In yet another embodiment, each $T^1$, $T^2$, and $T^3$ is $CR^1$, and $T^4$ is N.

In yet another embodiment, p in formula (8) is 0, $T^2$ and $T^3$ are C and $T^4$ is S.

In the above formula (9), each L and $L^1$ may be halo, tosylate, alkyl sulfonyl, carbonate, acetate, carbamate, trifluoroacetate, phosphate, methoxy or activated methoxy, nitro, boron, or a substituted boron such as boronate esters. Other leaving groups which may be suitable for use in the methods of the invention include but are not limited to sulfonate, sulfoxide, sulfone, acyloxy, phosphonate, imidazole, benzotriazole, or imide. In particular embodiments, each L and $L^1$ is halo.

In the above formula (10), W may be $OR^6$ and $R^6$ is a $C_{1-6}$ alkyl. Furthermore, the double bond linked to N in formula (10) may be delocalized, and the compound may be converted to its tautomeric isomer.

In the above formula (8) and (10), E together with N may be a 5-6 membered heteroaryl, or E may be selected from the group consisting of

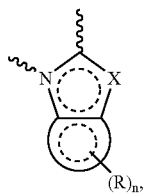
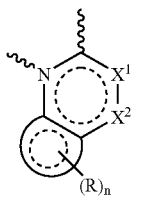

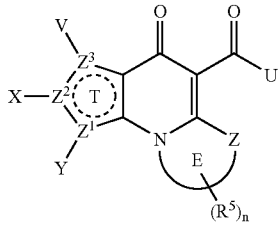

wherein X is O, S, CR$^1$ or NR$^1$;
X$^1$ and X$^2$ are independently CR$^1$ or NR$^1$;
each R$^1$ is H or C$_{1-6}$ alkyl;
R and n are as defined in formula (8).

In yet another aspect, the present invention provides a method for preparing a compound having formula (11):

(11)

and pharmaceutically acceptable salts, esters and prodrugs thereof;
wherein V, X, and Y are absent if attached to a heteroatom other than Nitrogen, and independently H, halo, azido, R$^2$, CH$_2$R$^2$, SR$^2$, OR$^2$ or NR$^1$R$^2$ when attached to C or N; or
wherein V and X, or X and Y may form a carbocyclic ring, heterocyclic ring, aryl or heteroaryl, each of which may be optionally substituted and/or fused with a cyclic ring;
Z$^1$, Z$^2$ and Z$^3$ are C, N, O or S;
Z is O, S, NR$^2$, CH$_2$ or C═O;
E together with N and Z forms an optionally substituted 5- or 6-membered ring that is fused to an optionally substituted aryl or heteroaryl, wherein said aryl or heteroaryl may be monocyclic or fused with a single or multiple ring, and wherein said single or multiple ring optionally contains one or more heteroatoms;
U is R$^2$, OR$^2$, NR$^1$R$^2$, NR$^1$—(CR$^1$$_2$)$_n$—NR$^3$R$^4$, SO$_3$R$^2$, SO$_2$NR$^1$R$^2$ or SO$_2$NR$^1$—(CR$^1$$_2$)$_n$—NR$^3$R$^4$;
wherein in each NR$^1$R$^2$, R$^1$ and R$^2$ together with N may form an optionally substituted ring;
in NR$^3$R$^4$, R$^3$ and R$^4$ together with N may form an optionally substituted ring;
R$^1$ and R$^3$ are independently H or C$_{1-6}$ alkyl;
each R$^2$ is H, or a C$_{1-10}$ alkyl or C$_{2-10}$ alkenyl each optionally substituted with a halogen, one or more non-adjacent heteroatoms selected from N, O and S, a carbocyclic ring, a heterocyclic ring, an aryl or heteroaryl, wherein each ring is optionally substituted; or R$^2$ is an optionally substituted carbocyclic ring, heterocyclic ring, aryl or heteroaryl; or R$^2$ is COR$^1$ or S(O)$_x$R$^1$ wherein x is 1-2;
R$^4$ is H, a C$_{1-10}$ alkyl or C$_{2-10}$ alkenyl optionally containing one or more non-adjacent heteroatoms selected from N, O and S, and optionally substituted with a carbocyclic or heterocyclic ring; or R$^3$ and R$^4$ together with N may form an optionally substituted ring;
each R$^5$ is a substituent at any position on W; and is H, OR$^2$, amino, alkoxy, amido, halogen, cyano or an inorganic substituent; or R$^5$ is C$_{1-6}$ alkyl, C$_{2-6}$ alkenyl, —CONHR$^1$, each optionally substituted by halo, carbonyl or one or more non-adjacent heteroatoms; or two adjacent R$^5$ are linked to obtain a 5-6 membered optionally substituted carbocyclic or heterocyclic ring, optionally fused to an additional optionally substituted carbocyclic or heterocyclic ring; and
n is 1-6.

In the above formula (11), ring T may form an optionally substituted 5-membered ring selected from the group consisting of:

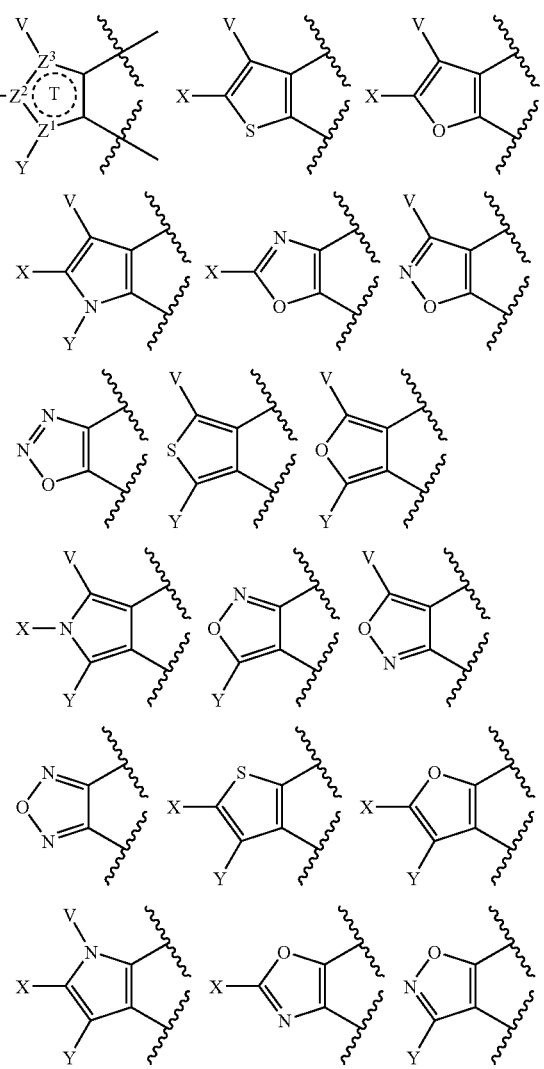

-continued

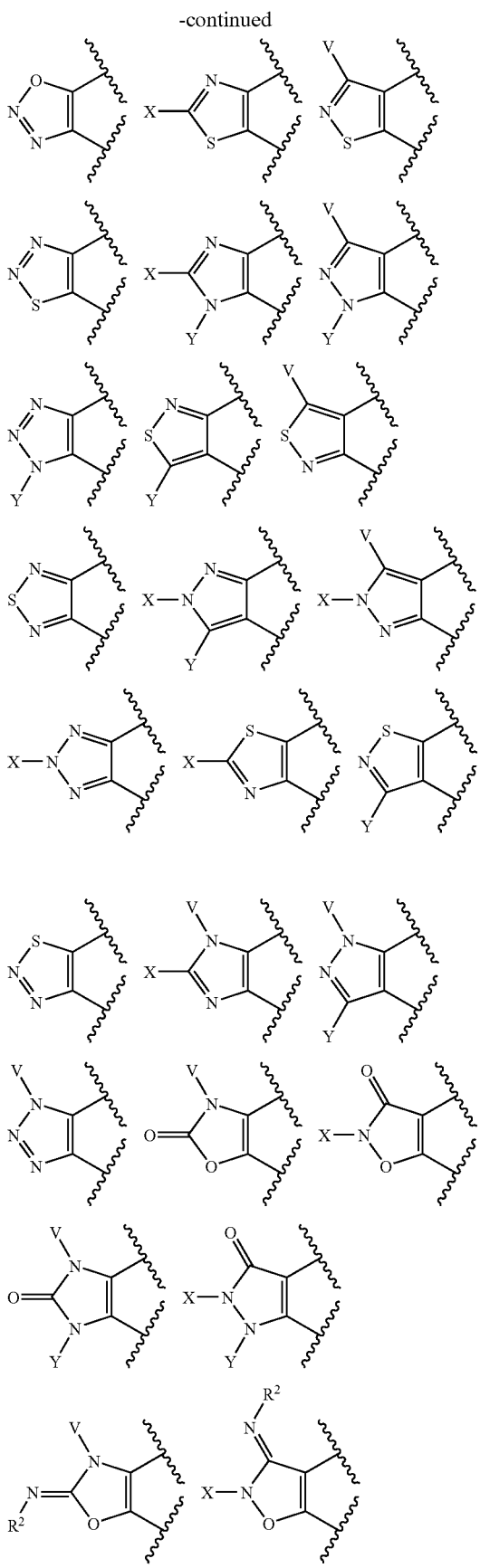

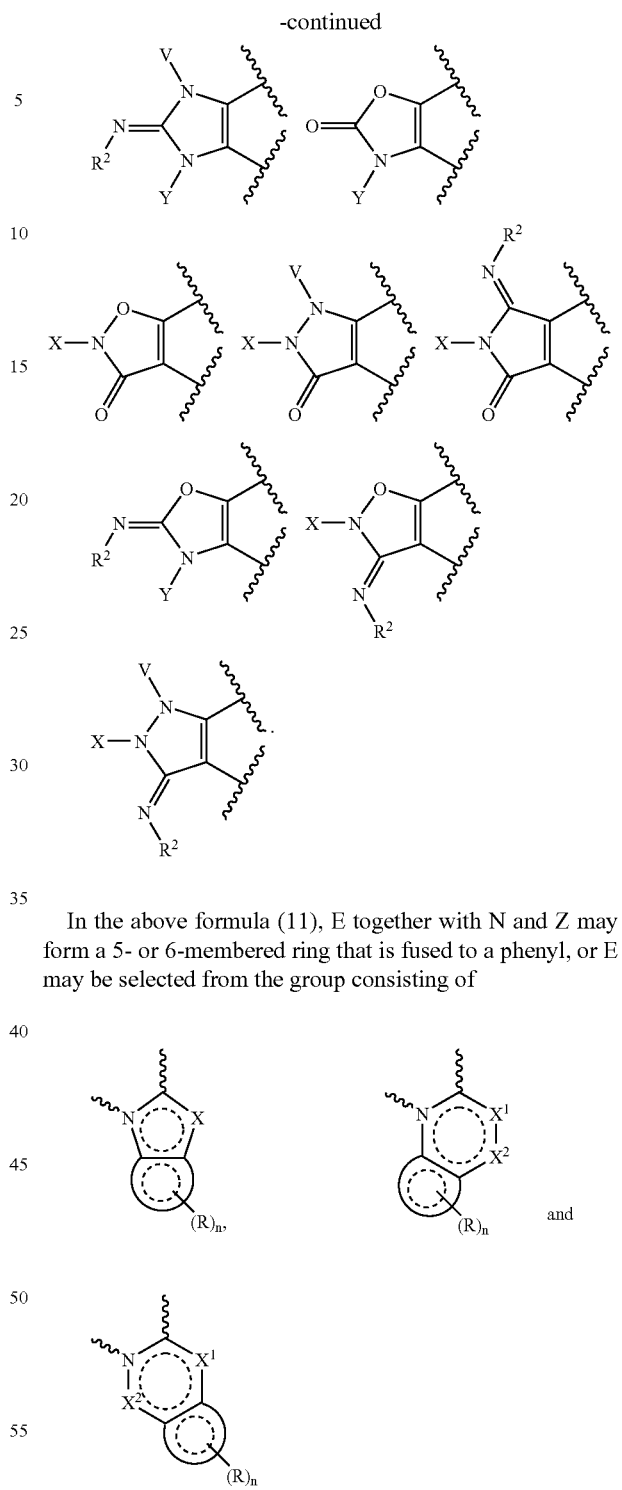

In the above formula (11), E together with N and Z may form a 5- or 6-membered ring that is fused to a phenyl, or E may be selected from the group consisting of

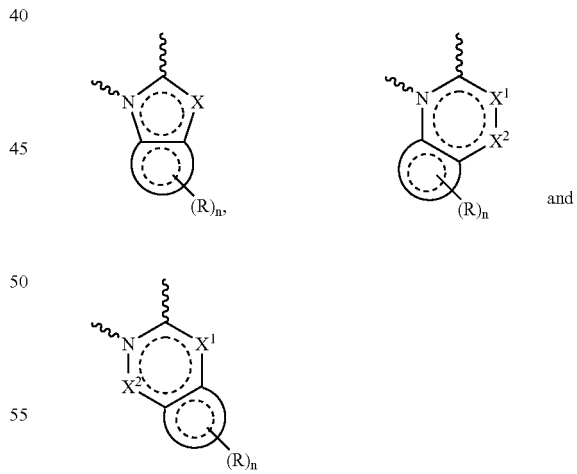

wherein X is O, S, $CR^1$ or $NR^1$;
$X^1$ and $X^2$ are independently $CR^1$ or $NR^1$;
each $R^1$ is H or $C_{1-6}$ alkyl;
R and n are as defined in formula (8).

In one embodiment, the methods of the invention may be used to prepare compounds having general formula (12A) or (12B):

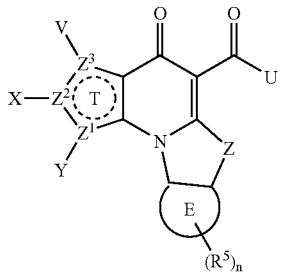

(12A)

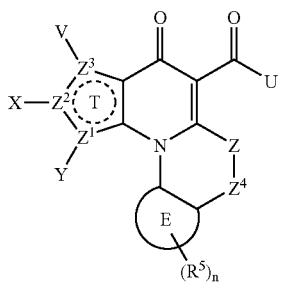

(12B)

wherein U, V, E, X, y, Z, $Z^1$, $Z^2$, $Z^3$, $R^5$ and n are as described in formula (11);

$Z^4$ is $CR^6$, $NR^2$, or C=O; and

Z and $Z^4$ may optionally form a double bond.

In yet another embodiment, the methods of the invention may be used to prepare compounds having general formula (13), (14) and (15)

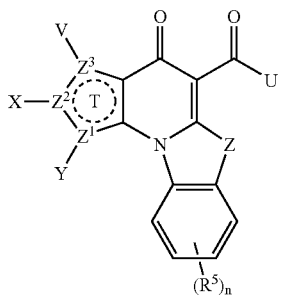

(13)

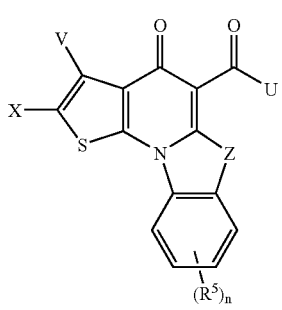

(14)

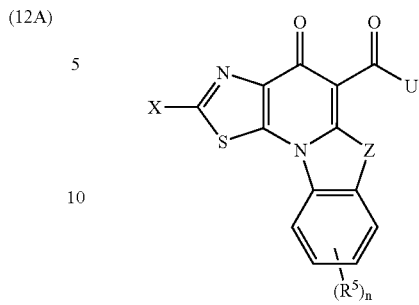

(15)

wherein U, V, X, Y, Z, $Z^1$, $Z^2$, $Z^3$, $R^5$ and n are as described in formula (11).

The compounds prepared according to the methods of the present invention are useful for ameliorating a cell proliferative disorder such as a tumor or a cancer; or are intermediates to such compounds. The cancer may be pancreatic cancer, including non-endocrine and endocrine tumors. Illustrative examples of non-endocrine tumors include but are not limited to adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor may be an islet cell tumor.

The compounds prepared according to the methods of the present invention are also useful for reducing cell proliferation and/or inducing cell death, such as apoptosis or apoptotic cell death, in a system or a subject; or are intermediates to such compounds. The system may be a cell or a tissue. In one embodiment, the system includes a pancreatic cell, such as a cell from a subject or a cultured cell (e.g., in vitro or ex vivo). In particular embodiments, the system includes a pancreatic cancer cell. In one embodiment, the system is a cell line such as PC3, HCT116, HT29, MIA Paca-2, HPAC, Hs700T, Panc 10.05, Panc 02.13, PL45, SW 190, Hs 766T, CFPAC-1 and PANC-1. The subject may be human or animal. Furthermore, the compounds prepared according to the methods of the present invention are useful for reducing microbial titers and/or for ameliorating a microbial infection; or are intermediates to such compounds. The microbial titers may be viral, bacterial or fungal titers.

DEFINITIONS

As used herein, the term "alkyl" refers to a carbon-containing compound, and encompasses groups containing one or more heteroatoms. The term "alkyl" also encompasses alkyls substituted with one or more substituents including but not limited to $OR^1$, amino, amido, halo, =O, aryl, heterocyclic groups, or inorganic substituents.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems.

As used herein, the term "aryl" refers to a polyunsaturated, typically aromatic hydrocarbon substituent, whereas a "heteroaryl" or "heteroaromatic" refer to an aromatic ring containing at least one heteroatom selected from N, O and S. The aryl and heteroaryl structures encompass compounds having monocyclic, bicyclic or multiple ring systems.

As used herein, the term "heteroatom" refers to any atom that is not carbon or hydrogen, such as nitrogen, oxygen or sulfur.

Illustrative examples of heterocycles include but are not limited to tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, 1,3-dihydrobenzimidazol-2-one, indole, thiazole, benzothiazole, thiadiazole, thiophene, tetrahydrothiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

As used herein, the term "Lewis acid" refers to any species that can accept an electron pair, such as metal ions and electron-deficient molecules. In one example, the methods of the present invention use a Lewis acid such as magnesium chloride. Other Lewis acids may be used in practicing the methods of the present invention, including species having the formula MLn, wherein L is a halogen atom or an organic radical such as an alkyl group, n is 3-5, and M is a group III elemental atom (e.g., B, Al, Ga, In), or a group IV elemental atom (e.g., Zr, Ti, Sn). Strong Lewis acidity is also observed for certain group V elemental atoms (e.g., As, Sb, V), and group VIII elemental atoms (e.g. Fe). Group II elemental atoms (e.g., Zn, Cd) generally display moderate Lewis acidity. Particular Lewis acids that may be used to practice the methods of the present invention include but are not limited to: $MgL_2$; $BL_3$; $AlL_3$; $FeL_3$; $GaL_3$; $SbL_5$; $InL_3$; $ZrL_4$; $SnL_4$; $TiL_4$; $TiL_3$; $AsL_3$; $SbL_3$. (See, e.g., D. P. N. Satchell & R. S. Satchell, Quantitative Aspects of the Lewis Acidity of Covalent Metal Halides and their Organo Derivatives, 69 CHEM. REV. 251, 253-55 (1969)).

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

DESCRIPTION OF THE INVENTION

The present invention relates to the preparation of compounds having any one of formula (1), (2A), (2B), (4), (4A), (4B), (5A), (5B), (8), (11), (12A), (12B) and 13-15 and pharmaceutically acceptable salts, esters, and prodrugs thereof. The compounds may interact with regions of DNA that can form quadruplexes, and may also be used for treatment of cell proliferative disorders.

In one aspect, the present invention provides a method for preparing a compound having formula 1:

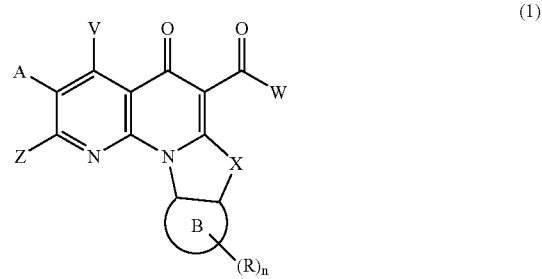

(1)

and pharmaceutically acceptable salts, esters and prodrugs thereof, wherein:

A, V, and Z are independently H, halo, cyano, $R^2$, $CH_2R^2$, $SR^2$, $OR^2$ or $NR^1R^2$; or wherein A and Z, or V and Z may form a carbocyclic ring, heterocyclic ring, aryl or heteroaryl, each of which may be optionally substituted and/or fused with a cyclic ring;

W is $NR^1R^2$ or $OR^6$ wherein $R^6$ is a $C^{1-10}$ alkyl;

X is O, S, $CR^1$ or $NR^1$;

each $R^1$ is H or a $C_{1-6}$ alkyl;

each $R^2$ is H, or a $C_{1-10}$ alkyl or $C_{2-10}$ alkenyl each optionally substituted with a halogen, one or more non-adjacent heteroatoms, a carbocyclic ring, a heterocyclic ring, an aryl or heteroaryl, wherein each ring is optionally substituted;

R is a substituent at any position on B; and is H, $OR^2$, amino, alkoxy, amido, halogen, cyano or an inorganic substituent; or R is $C_{1-6}$ alkyl, $C_{2-6}$ alkenyl, —$CONHR^1$, each optionally substituted by one or more non-adjacent heteroatoms; or two adjacent R are linked to obtain a 5-6 membered optionally substituted carbocyclic or heterocyclic ring, optionally fused to an additional optionally substituted carbocyclic or heterocyclic ring;

B is an optionally substituted ring, which may be aromatic or nonaromatic, and may be monocyclic or fused with a single or multiple ring, wherein said single or multiple ring may optionally contain one or more heteroatoms;

n is 1-6;

or a compound having formula (2A) or (4A):

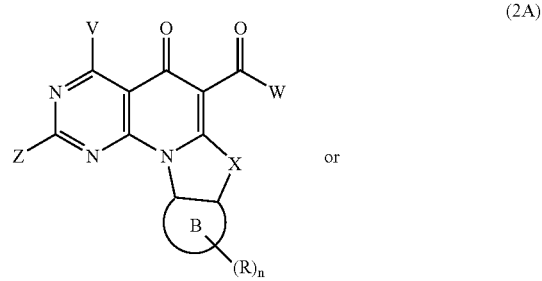

(2A)

or

-continued

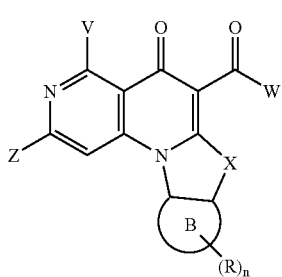
(4A)

wherein n, V, Z, X, W, B and R are as defined in formula (1), comprising:

contacting a compound having formula (6A), (6B) or (6C)

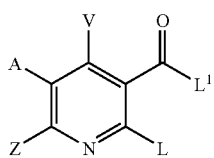
(6A)

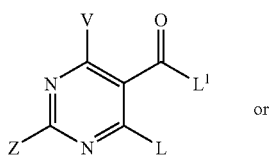
(6B)

or

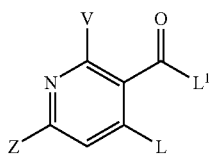
(6C)

wherein each L and $L^1$ is a leaving group; and A, V, and Z are as defined in formula (1);

with a compound having formula (7) and tautomers thereof

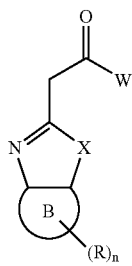
(7)

wherein n, X, B and R are as defined in formula (1); and W is $OR^6$ wherein $R^6$ is a $C_{1-10}$ alkyl; or W is $NR^1R^2$, wherein $R^1$ and $R^2$ are as defined in formula (1);

wherein said compound having formula (6A), (6B) or (6C) is contacted with said compound having formula (7) and tautomers thereof in the presence of a base to produce a compound having formula (1), and optionally hydrolyzing said compound of formula (1).

In another aspect, the present invention provides methods for preparing a compound having formula (8)

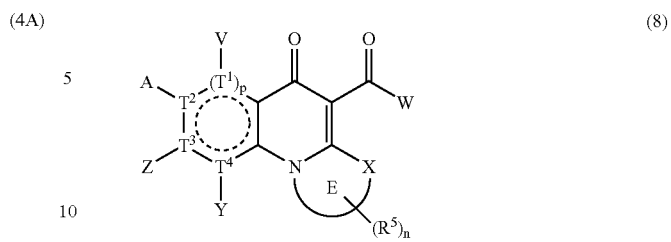
(8)

wherein V, A, Z, and Y when attached to C are independently H, halo, azido, $R^2$, $CH_2R^2$, $SR^2$, $OR^2$, $NR^1R^2$; or absent when attached to N;

$T^1$, $T^2$, $T^3$, and $T^4$ are independently C, N or S;

W is $NR^1R^2$ or $OR^6$, wherein $R^6$ is a $C_{1-10}$ alkyl;

X is O, S, $CR^1$ or $NR^1$;

E together with N and X form a ring, which may be fused with a single or multiple ring, wherein the single or multiple ring optionally contains one or more heteroatoms;

n is 1-6;

p is 0-1;

each $R^1$ is H or a $C_{1-6}$ alkyl;

each $R^2$ is H, or a $C_{1-10}$ alkyl or $C_{2-10}$ alkenyl each optionally substituted with a halogen, one or more non-adjacent heteroatoms, a carbocyclic ring, a heterocyclic ring, an aryl or heteroaryl, wherein each ring is optionally substituted;

$R^5$ is a substituent at any position on E; and is H, $OR^2$, amino, alkoxy, amido, halogen, cyano or an inorganic substituent; or R is $C_{1-6}$ alkyl, $C_{2-6}$ alkenyl, —$CONHR^1$, each optionally substituted by one or more non-adjacent heteroatoms; or two adjacent $R^5$ are linked to obtain a 5-6 membered optionally substituted carbocyclic or heterocyclic ring, optionally fused to an additional optionally substituted carbocyclic or heterocyclic ring;

comprising contacting a compound having a formula (9) with a compound having formula (10) and tautomers thereof:

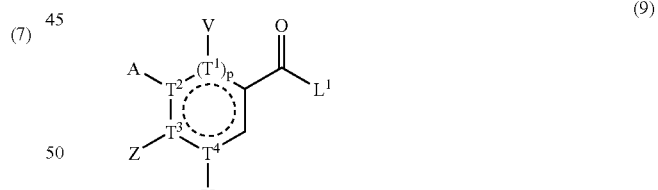
(9)

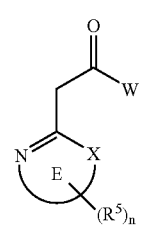
(10)

wherein n, V, A, Z, Y, $T^1$, $T^2$, $T^3$, $T^4$, X, W, E and $R^5$ are as defined in formula (8); and each L and $L^1$ is a leaving group.

In the above methods, the reagents in the presence of a base and coordinating atom, such as the coordinating atom of a Lewis acid. Although the mechanism is not necessary to practice the invention, the use of a co-ordinating metal or acid allows the hydrogen on the α-carbon in formula (7) and (10) to become more acidic, thus facilitating its removal by a weak base (in this case a trialkylamine base). Hence the anion (reactive intermediate) can be generated under more mild conditions and reacted with the other reactant. The coordinating metal then orientates (holds) the resulting products in a conformation which facilitates the second bond formation allowing it to occur under milder conditions. In this step, again the remaining hydrogen on the α-carbon is rendered more acidic, and the molecule is in a conformation in which the reactive atoms are held more closely together, helping overcome entropic barriers.

The compounds of the present invention having formula (1), (2A), (2B), (4), (4A), (4B), (5A), (5B), (8), (11), (12A), (12B) and 13-15 are reproduced below:

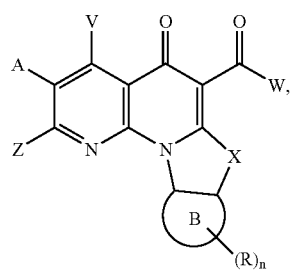
(1)

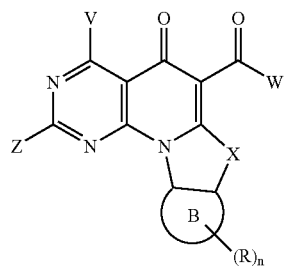
(2A)

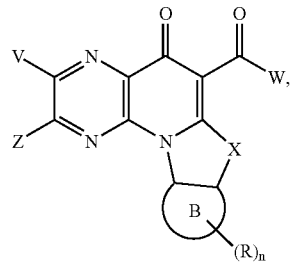
(2B)

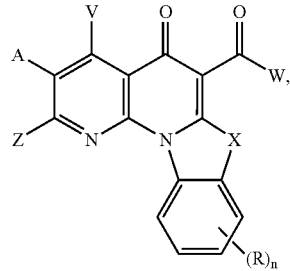
(4)

-continued

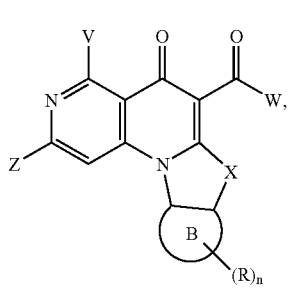
(4A)

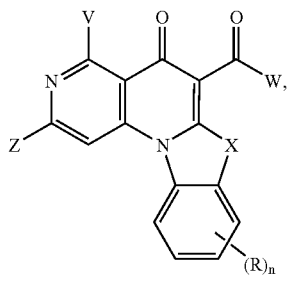
(4B)

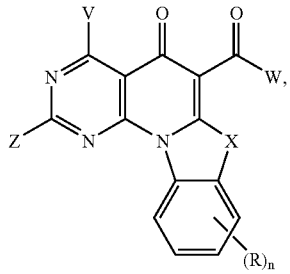
(5A)

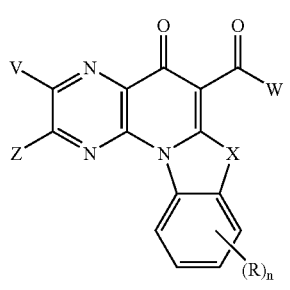
(5B)

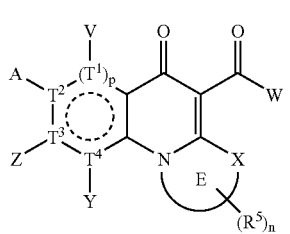
(8)

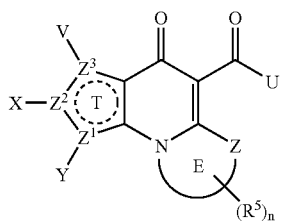
(11)

-continued

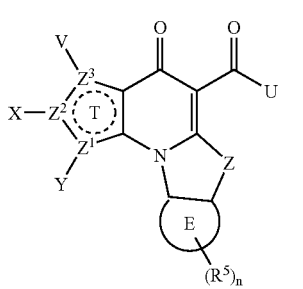
(12A)

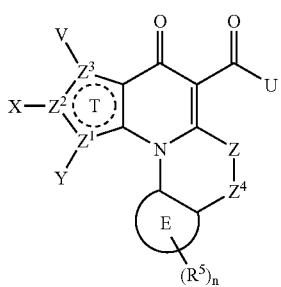
(12B)

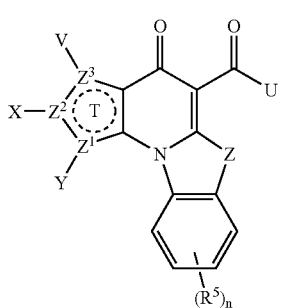
(13)

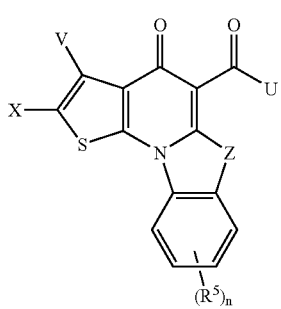
(14)

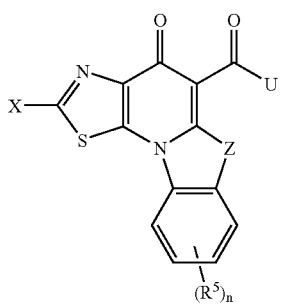
(15)

wherein each substituent is as defined above.
In the above formula (4), X may be $NR^1$;
A and V may independently be H or halo;
Z may be an optionally substituted carbocyclic ring, heterocyclic ring, aryl, or heteroaryl; and R may be a substituent at any position on the fused ring; and is H, $OR^2$, cyano, halo, or an inorganic substituent; or $C_{1-6}$ alkyl, $C_{2-6}$ alkenyl, $C_{3-7}$ cycloalkyl, each optionally substituted by halo, =O or one or more heteroatoms.

In the above formula (4), Z may be a 5-6 membered heterocyclic ring containing N, O, or S, and optionally substituted with halo, alkyl, alkoxy, or acetyl.

In each of the above formula, ring B in formula (1), (2A), (2B), (4A), (7) or (8), or ring E in formula (11), (12A) and (12B) may be selected from the group consisting of:

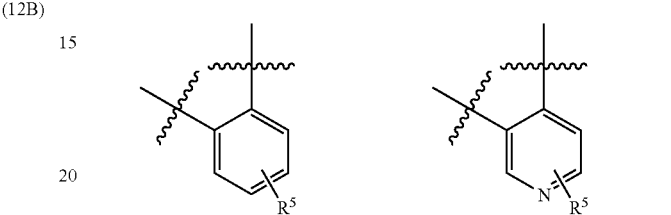

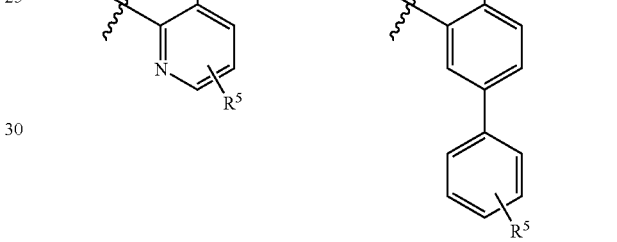

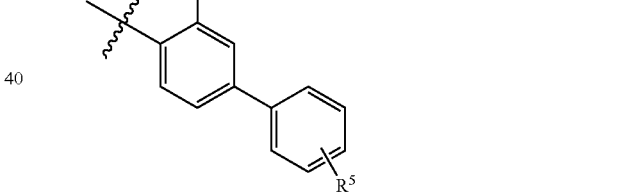

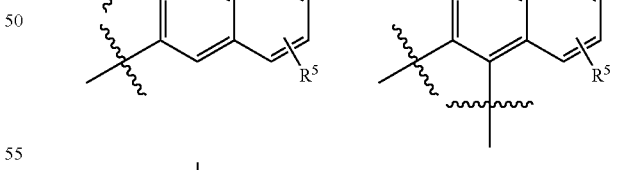

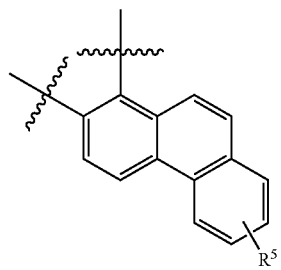

-continued
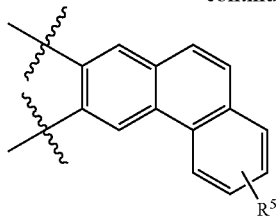
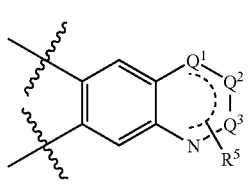
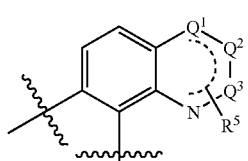
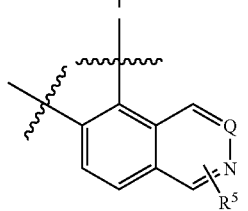
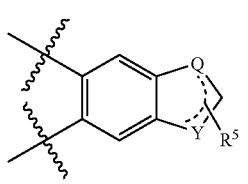
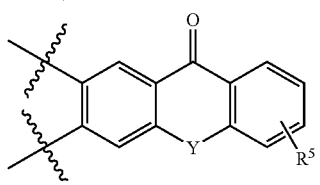
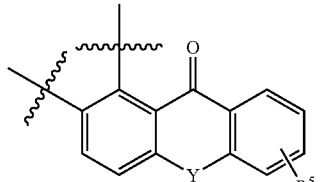
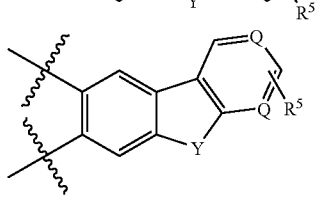
-continued
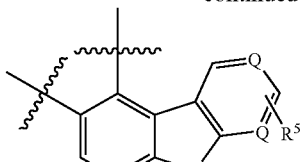
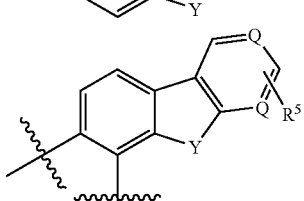
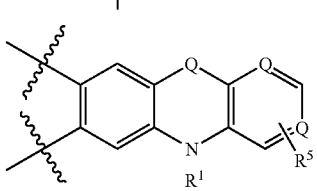
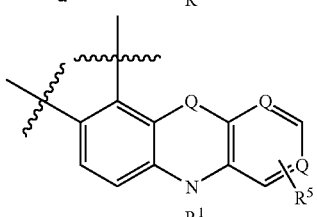
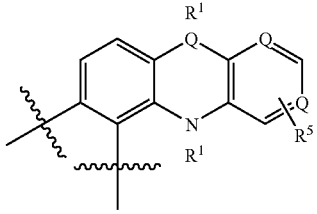
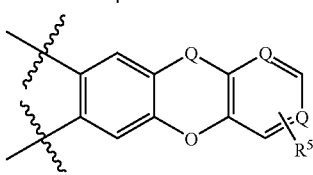
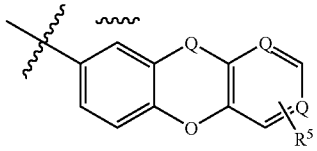
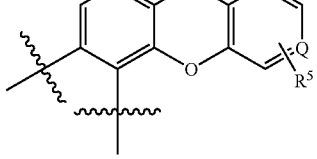
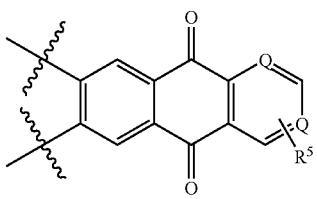

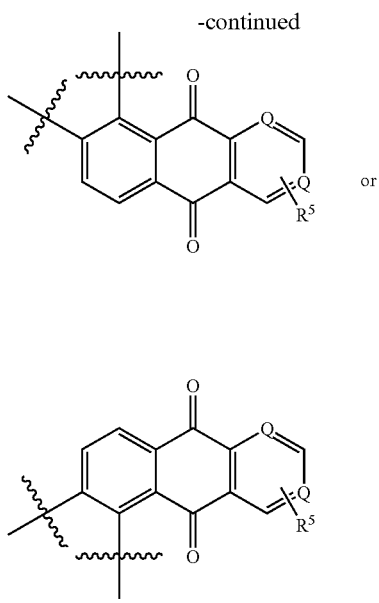

wherein each Q, $Q^1$, $Q^2$, and $Q^3$ is independently CH or N; Y is independently O, CH, C=O or $NR^1$;
$R^1$ is as defined in formula (1); and
$R^5$ is a substituent at any position on ring B or E; and is H, $OR^2$, amino, alkoxy, amido, halogen, cyano or an inorganic substituent; or R is $C_{1-6}$ alkyl, $C_{2-6}$ alkenyl, —$CONHR^1$, each optionally substituted by one or more non-adjacent heteroatoms; or two adjacent $R^5$ are linked to obtain a 5-6 membered optionally substituted carbocyclic or heterocyclic ring, optionally fused to an additional optionally substituted carbocyclic or heterocyclic ring.

In one embodiment, B or E is an optionally substituted phenyl. In particular examples, each $R^5$ in each of the above formula is H or halo.

In each of the above formula, one of A (if present) or V may be H or halo. In particular examples, one of A or V may be H or fluoro.

In each of the above formula, Z may be H, halo, or $SR^2$, wherein $R^2$ is a $C_{1-10}$ alkyl or $C_{2-10}$ alkenyl optionally substituted with a heteroatom, a carbocyclic ring, a heterocyclic ring, an aryl or a heteroaryl. In one example, $R^2$ is a $C_{1-10}$ alkyl.

In each of the above formula, X may be $NR^1$ or S.

In some embodiments, Z, A, and V in each of the above formula may be independently H. In other embodiments, two of A, Z and V are H, and sometimes only one of A, Z and V is H. In certain embodiments, only one of A, Z and V is a halogen (e.g., fluorine), and sometimes two of A, Z and V are halogen. In other embodiments, Z, A and V in each of the above formula is $SR^2$, which may be oxidized to $SO_2R$, which can readily be replaced with another nucleophile, such as OR or an amino group.

In some embodiments, W is $OR^6$ group, which may be replaced with a —$R^7R^8$—$(CH_2)_n$—$CHR^2$—$NR^3R^4$, wherein $R^7$ is N or $CR^1$ wherein $R^1$ is H or $C_{1-6}$ alkyl; $R^8$ is H or $C_{1-10}$ alkyl, and wherein in the —$CHR^2$—$NR^3R^4$ moiety, one of $R^3$ or $R^4$ together with the C may form an optionally substituted heterocyclic or heteroaryl ring, or wherein in the —$CHR^2$—$NR^3R^4$ moiety each $R^3$ or $R^4$ together with the N may form an optionally substituted carbocyclic, heterocyclic, aryl or heteroaryl ring. In some embodiment, W is not $NH_2$.

In each of the above formula, one, two, three or all of V, Z, and A (if present) may independently be selected from a $NR^1R^2$ moiety, wherein $R^1$ is H, and $R^2$ is a $C_{1-10}$ alkyl optionally substituted with a heteroatom, a $C_{3-6}$ cycloalkyl, aryl or a 5-14 membered heterocyclic ring containing one or more N, O, or S. In some embodiments, W is a $NR^1R^2$ moiety and one of A or Z is the same or a different $NR^1R^2$ moiety compared to W. If more than one $NR^1R^2$ moiety is present in a compound within the invention, as when both A and W are $NR^1R^2$ in a compound according to formula (1), for example, each $R^1$ and each $R^2$ are independently selected.

In one example, $R^2$ is a $C_{1-10}$ alkyl substituted with an optionally substituted 5-14 membered heterocyclic ring. For example, $R^2$ may be a $C_{1-10}$ alkyl substituted with morpholine, thiomorpholine, imidazole, aminothiadiazole, pyrrolidine, piperazine, pyridine or piperidine. Alternatively, $R^1$ and $R^2$ together with N may form an optionally substituted heterocyclic ring containing one or more N, O, or S. For example, $R^1$ and $R^2$ together with N may form piperidine, pyrrolidine, piperazine, morpholine, thiomorpholine, imidazole, or aminothiadiazole.

Illustrative examples of optionally substituted heterocyclic rings include but are not limited to tetrahydrofuran, 1,3-dioxolane, 2,3-dihydrofuran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, aminothiadiazole, imidazolidine-2,4-dione, benzimidazole, 1,3-dihydrobenzimidazol-2-one, indole, thiazole, benzothiazole, thiadiazole, thiophene, tetrahydro-thiophene 1,1-dioxide, diazepine, triazole, diazabicyclo[2.2.1]heptane, 2,5-diazabicyclo[2.2.1]heptane, and 2,3,4,4a,9,9a-hexahydro-1H-β-carboline.

In each of the above formula, each optionally substituted moiety may be substituted with one or more halo, $OR^2$, $NR^1R^2$, carbamate, $C_{1-10}$ alkyl, $C_{2-10}$ alkenyl, each optionally substituted by halo, C=O, aryl or one or more heteroatoms; inorganic substituents, aryl, carbocyclic or a heterocyclic ring.

The compounds of the present invention may be chiral. As used herein, a chiral compound is a compound that is different from its mirror image, and has an enantiomer. Furthermore, the compounds may be racemic, or an isolated enantiomer or stereoisomer. Methods of synthesizing chiral compounds and resolving a racemic mixture of enantiomers are well known to those skilled in the art. See, e.g., March, "Advanced Organic Chemistry," John Wiley and Sons, Inc., New York, (1985), which is incorporated herein by reference.

Illustrative examples of compounds which may be prepared using the methods of the invention are shown in Table 1, and in the Examples. The present invention also encompasses other compounds having any one of the formula (1), (2), (2A), (2B), (4), (4A), (4B), (5A), (5B) (8), (11), (12A), (12B) and 13-15 comprising substituents V, A, Z, Y, and W independently selected from the substituents exemplified in Table 1 and in the Examples. Thus, the present invention is not limited to the specific combination of substituents described in various embodiments below.

TABLE 1

| Structure | MS | Yield: |
|---|---|---|
| | 325.3 | 77% |
| | 359.3 (M + H)+ | 76% |
| | 369.3 (M + H)+ | 62% |
| | 359.3 (M + H)+ | 90% (2:1 mix) |
| | 411.2 (M + H)+ | 56% |

TABLE 1-continued

| Structure | Structure | MS | Yield: |
|---|---|---|---|
| (structure) | (structure) | 356.3 (M + H)⁺ | 92% |
| (structure) | | 356.4 (M + H)⁺ | 90% |
| (structure) | | 392.2 (M + H)⁺ | 95% |
| (structure) | | 372.1 (M + H)⁺ | 98% |
| (structure) | | 392.2 (M + H)⁺ | 90% |

TABLE 1-continued

| Structure | MS | Yield: |
|---|---|---|
| (structure) | 411.3 (M + H)+ | 76% |
| (structure) | 394.4 | 60% |
| (structure) | 289.2 | 84% |
| (structure) | 409.3 | 89% |
| (structure) | 377.4 | 68% |

TABLE 1-continued

|  | MS | Yield: |
|---|---|---|
|  | 353.2 | 12% |
|  | 377.3 | 97% |
|  | 306.7 | 10% |
|  | 381.0 | 68% |
|  | 392.2 | 97% |

TABLE 1-continued
| | MS | Yield: |
|---|---|---|
| 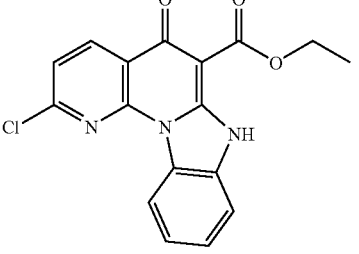 | 342.2 | 41% |
| 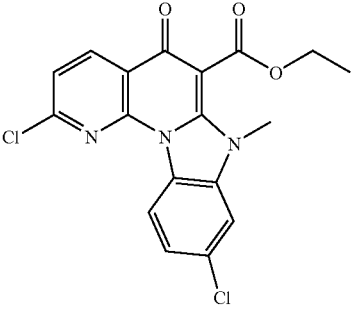 | 390 | 73% |
| 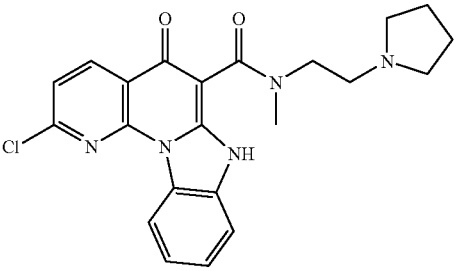 | 424.1 | 43% |
| 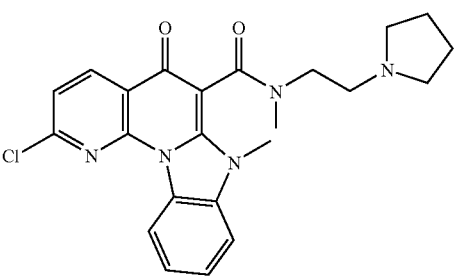 | 438.6 | 62% |
| 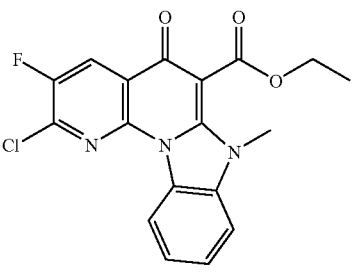 | 374.5 | 45% |

TABLE 1-continued

| Structure | MS | Yield: |
|---|---|---|
| (chloro-thieno-benzothiazole ethyl ester structure) | 364.2 | 56% |
| (thieno-naphtho-imidazole ethyl ester structure) | 363.2 | 34% |
| (thieno-benzothiazole ethyl ester structure) | 330.0 | 44% |
| (thieno-benzimidazole ethyl ester structure) | 313.1 | 29% |

The compounds described herein may interact with regions of DNA that can form quadruplexes; or are useful intermediates to such compounds. Because regions of DNA that can form quadruplexes are regulators of biological processes such as oncogene transcription, modulators of quadruplex biological activity can be utilized as cancer therapeutics. Molecules that interact with regions of DNA that can form quadruplexes can exert a therapeutic effect on certain cell proliferative disorders and related conditions. Particularly, abnormally increased oncogene expression can cause cell proliferative disorders, and quadruplex structures typically down-regulate oncogene expression. Examples of oncogenes include but are not limited to MYC, HIF, VEGF, ABL, TGF, PDGFA, MYB, SPARC, HUMTEL, HER, VAV, RET, H-RAS, EGF, SRC, BCL1, BCL2, DHFR, HMGA, and other oncogenes known to one of skill in the art. Furthermore, the compounds described may induce cell death (e.g., apoptosis) and not interact with regions of DNA that can form quadruplexes; or are useful intermediates to such compounds.

Molecules that bind to regions of DNA that can form quadruplexes can exert a biological effect according to different mechanisms, which include for example, stabilizing a native quadruplex structure, inhibiting conversion of a native quadruplex to duplex DNA by blocking strand cleavage, and stabilizing a native quadruplex structure having a quadruplex-destabilizing nucleotide substitution and other sequence specific interactions. Thus, compounds that bind to regions of DNA that can form quadruplexes described herein may be administered to cells, tissues, or organisms for the purpose of down-regulating oncogene transcription and thereby treating cell proliferative disorders.

Determining whether the biological activity of native DNA that can form quadruplexes is modulated in a cell, tissue, or organism can be accomplished by monitoring quadruplex biological activity. Quadruplex forming regions of DNA biological activity may be monitored in cells, tissues, or organisms, for example, by detecting a decrease or increase of gene transcription in response to contacting the quadruplex forming DNA with a molecule. Transcription can be detected by directly observing RNA transcripts or observing polypeptides translated by transcripts, which are methods well known in the art.

Molecules that interact with quadruplex forming DNA and quadruplex forming nucleic acids can be utilized to treat many cell proliferative disorders. Cell proliferative disorders include, for example, colorectal cancers and hematopoietic neoplastic disorders (i.e., diseases involving hyperplastic/neoplastic cells of hematopoietic origin such as those arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (Vaickus, Crit. Rev. in Oncol./Hemotol. 11:267-297 (1991)). Lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL); cutaneous T-cell lymphoma (CTCL), large granular lymphocytic leukemia (LGF), Hodgkin's disease and Reed-Sternberg disease. Cell proliferative disorders also include cancers of the colorectum, breast, lung, liver, pancreas, lymph node, colon, prostate, brain, head and neck, skin, liver, kidney, and heart. Compounds that interact with regions of DNA that may form quadruplexes also can be utilized to target cancer related processes and conditions, such as increased angiogenesis, by inhibiting angiogenesis in a subject.

Compounds that interact with quadruplex forming regions of DNA can also be used to reduce a microbial infection, such as a viral infection. Retroviruses offer a wealth of potential targets for G-quadruplex targeted therapeutics. G-quadruplex structures have been implicated as functional elements in at least two secondary structures formed by either viral RNA or DNA in HIV, the dimer linker structure (DLS) and the central DNA flap (CDF). Additionally, DNA aptamers which are able to adopt either inter- or intramolecular quadruplex structures are able to inhibit viral replication. In one example, DNA aptamers are able to inhibit viral replication by targeting the envelope glycoprotein (putatively). In another example, DNA aptamers inhibit viral replication by targeting the HIV-integrase respectively, suggesting the involvement of native quadruplex structures in interaction with the integrase enzyme.

Dimer linker structures, which are common to all retroviruses, serve to bind two copies of the viral genome together by a non-covalent interaction between the two 5' ends of the two viral RNA sequences. The genomic dimer is stably associated with the gag protein in the mature virus particle. In the case of HIV, the origin of this non-covalent binding may be traced to a 98 base-pair sequence containing several runs of at least two consecutive guanines (e.g., the 3' for the formation of RNA dimers in vitro). An observed cation (potassium) dependence for the formation and stability of the dimer in vitro, in addition to the failure of an antisense sequence to effectively dimerize, has revealed the most likely binding structure to be an intermolecular G-quadruplex.

Prior to integration into the host genome, reverse transcribed viral DNA forms a pre-integration complex (PIC) with at least two major viral proteins, integrase and reverse transcriptase, which is subsequently transported into the nucleus. The Central DNA Flap (CDF) refers to 99-base length single-stranded tail of the + strand, occurring near the center of the viral duplex DNA, which is known to a play a role in the nuclear import of the PIC. Oligonucleotide mimics of CDF are known to form intermolecular G-quadruplex structures in cell-free systems.

Thus, compounds that recognize quadruplex forming regions can be used to stabilize the dimer linker structure and thus prevent de-coupling of the two RNA strands. Also, by binding to the quadruplex structure formed by the CDF, protein recognition and/or binding events for nuclear transport of the PIC may be disrupted. In either case, a substantial advantage can exist over other anti-viral therapeutics. Current Highly Active Anti-Retroviral Therapeutic (HAART) regimes rely on the use of combinations of drugs targeted towards the HIV protease and HIV integrase. The requirement for multi-drug regimes is to minimize the emergence of resistance, which will usually develop rapidly when agents are used in isolation. The source of such rapid resistance is the infidelity of the reverse transcriptase enzyme which makes a mutation approximately once in every 10,000 base pairs. An advantage of targeting viral quadruplex structures over protein targets, is that the development of resistance is slow or is impossible. A point mutation of the target quadruplex can compromise the integrity of the quadruplex structure and lead to a non-functional copy of the virus. A single therapeutic agent based on this concept may replace the multiple drug regimes currently employed, with the concomitant benefits of reduced costs and the elimination of harmful drug/drug interactions.

The following examples are offered to illustrate but not to limit the invention.

EXAMPLE 1

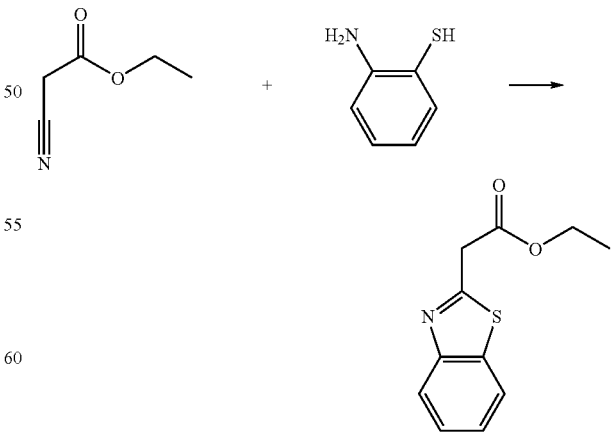

Ethyl 2-(benzothiazol-2-yl)acetate was prepared by the method of Abbotto, Bradamante et. al. ( J. Org. Chem. 2002, 16, 5753). A neat mixture of 2-aminothiophenol (6.94 g, 50 mmol) and ethyl cyanoacetate (5.65 g, 50 mmol) was heated at 120° C. for 3 hours at which time TLC analysis indicated that the reaction was complete as judged by the disappearance of starting material. The dark orange mixture was diluted with ethyl acetate/hexanes and purified by flash chromatography using 10-20% ethyl acetate/hexanes (R$_f$0.35, 10% ethyl acetate/hexanes) as an eluant. After concentration by rotary evaporator, ethyl 2-(benzothiazol-2-yl)acetate could be obtained as a yellow oil in 72% yield (7.97 g). LCMS: 222.3 (M+H)$^+$.

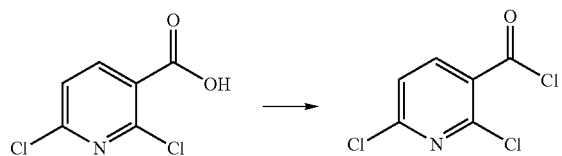

2,6-dichloropicolinic acid (2.70 g, 11 mmol) was suspended in dichloromethane (10 mL) and treated with oxalyl chloride (1.74 g, 14 mmol). The mixture was cooled in an ice bath and 2 drops of dimethylformamide was added. After an initial vigorous outgassing, the ice bath was removed and the solution was stirred for 18 hours at room temperature. An aliquot was quenched with methanol and analyzed by LCMS indicating that all the acid had been converted to the acid chloride. The solution was concentrated on a rotary evaporator to give the acid chloride as a light brown crystalline solid which was used in the subsequent step without further purification. LCMS: 206.2 (methyl ester M+H)$^+$.

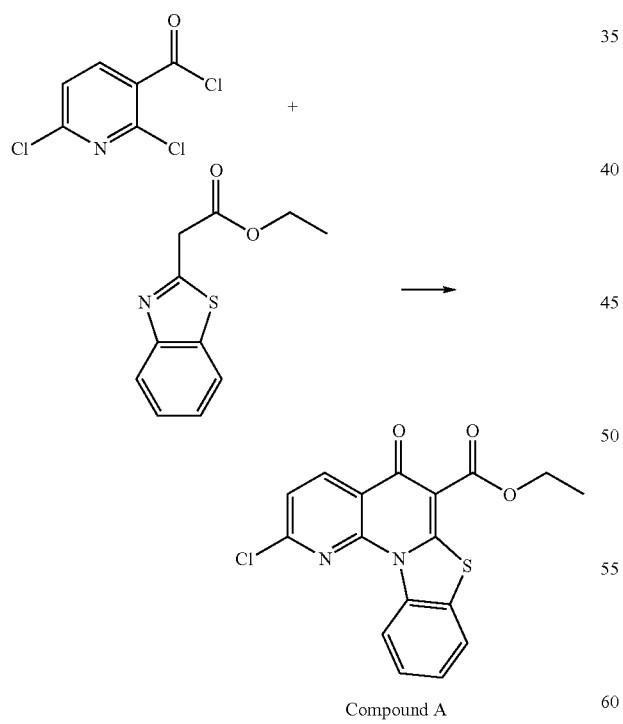

Compound A

Tetrahydrofuran (25 mL) was added to a mixture of ethyl 2-(benzothiazol-2-yl)acetate, magnesium chloride (2.21 g, 10 mmol) and 2,6-dichloropicolinyl chloride (11 mmol). The resulting suspension was cooled in an ice bath and triethylamine (2.02 g, 20 mmol) was added dropwise at such a rate that the internal temperature did not go over 10° C. as measured with an internal thermocouple probe. Once the addition was complete, the ice bath was removed and the mixture was allowed to stir while warming to room temperature. Although certain adducts require additional heat and/or base to produce the cyclization, this example with 2,6-dichloropicolinic acid chloride cyclized spontaneously such that after 5 hours of stirring at room temperature, compound A could be isolated by diluting the reaction mixture with water, extraction with dichloromethane (2×150 ml) and drying the resulting organic phase with sodium sulfate. Purification by trituration with diethyl ether yielded 2.71 g (76% based on ethyl 2-(benzothiazol-2-yl)acetate) as fluffy beige crystals. $^1$HNMR (CDC13, 400 MHz) 9.55 (1H, d, 8.4 Hz), 8.86 (1H, d, 8.4 Hz), 7.77 (1H, dd, 7.6, 1.2 Hz), 7.61 (1H, m), 7.56 (1H, d, 8.4 Hz), 7.49 (1H, m), 4.53 (2H, q, 7.2 Hz), 1.50 (3H, t, 7.2 Hz) $^{13}$CNMR (CDC13, 100 MHz) 171.1, 167.4, 163.1, 152.9, 148.4, 140.5, 137.7, 128.5, 127.8, 126.6, 123.1, 122.1, 121.7, 120.5, 106.3, 62.0, 14.7 LCMS: 359.3 (M+H)$^+$.

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

The invention claimed is:

1. A method for preparing a compound having formula 1:

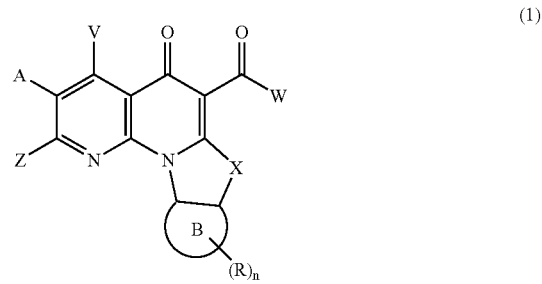

(1)

or a pharmaceutically acceptable salt thereof, wherein:
A, V, and Z are independently H, halo, azido, R$^2$, CH$_2$R$^2$, SR$^2$, OR$^2$ or NR$^1$R$^2$;
W is NR$^1$R$^2$ or OR$^6$ wherein R$^6$ is a C$_{1-10}$ alkyl;
X is S;
each R$^1$ is H or a C$_{1-6}$ alkyl;
each R$^2$ is H, or a C$_{1-10}$ alkyl or C$_{2-10}$ alkenyl each optionally substituted with a halogen, a carbocyclic ring, or a heterocyclic ring, wherein each ring is optionally substituted; or
R$^1$ and R$^2$ together with N may form an optionally substituted heterocyclic ring containing one or more N, O, or S;
R is a substituent at any position on ring B'; and is H, OR$^2$, amino, alkoxy, amido, halogen, or cyano; or R is C$_{1-6}$ alkyl, C$_{2-6}$ alkenyl, or —CONHR$^1$;

B' is an optionally substituted phenyl ring; and
n is 0-4;
comprising:
contacting a compound having formula (6A)

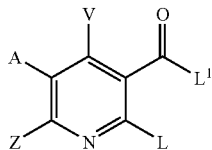
(6A)

wherein each L and L¹ is a leaving group; and A, V, and Z are as defined in formula (1);
with a compound having formula (7) or tautomers thereof

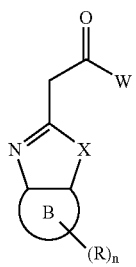
(7)

wherein n, X, B' and R are as defined in formula (1); and W is $OR^6$ wherein $R^6$ is a $C_{1-10}$ alkyl; or W is $NR^1R^2$, wherein $R^1$ and $R^2$ are as defined in formula (1);
wherein said compound having formula (6A) is contacted with said compound having formula (7) or tautomers thereof in the presence of a non-nucleophilic base to produce a compound having formula (1);
and wherein each optionally substituted group is unsubstituted or is substituted with one or more halo, $OR^2$, $NR^1R^2$, $C_{1-10}$ alkyl, $C_{2-10}$ alkenyl, each optionally substituted by halo, or aryl ; or a carbocyclic or a heterocyclic ring;
where $R^1$ and $R^2$ are as defined above.

2. The method of claim 1, wherein W in formula (1) is $OR^6$, and $R^6$ is a $C_{1-6}$ alkyl.

3. The method of claim 2, further comprising the step of contacting said compound having formula (1) with an amine of the formula $$HNR^1—(CR^1{}_2)n—NR^3R^4 \quad (3)$$

wherein $R^1$ and $R^3$ are independently H or $C_{1-6}$ alkyl;
n is 1-6; and
$R^4$ is H, a $C_{1-10}$ alkyl or $C_{2-10}$ alkenyl optionally substituted with a carbocyclic or heterocyclic ring; or $R^3$ and $R^4$ together with N may form an optionally substituted ring containing one or more N, O or S.

4. The method of claim 3, wherein $R^3$ and $R^4$ together with N form an optionally substituted piperidinyl, pyrrolidinyl, piperazinyl, morpholinyl, thiomorpholinyl, imidazolyl, or aminothiadiazolyl ring.

5. The method of claim 2, further comprising the step of contacting said compound having formula (1) with an amine of the formula $HNR^1R^2$, provided said amine is not $NH_3$.

6. The method of claim 5, wherein $R^1$ is H, and $R^2$ is a $C_{1-10}$ alkyl optionally substituted with a $C_{3-6}$ cycloalkyl, aryl or a 5-14 membered heterocyclic ring containing one or more N, O or S; or $R^1$ and $R^2$ together with N may form an optionally substituted heterocyclic ring containing one or more N, O or S.

7. The method of claim 6, wherein $R^2$ is a $C_{1-10}$ alkyl substituted with a morpholinyl, thiomorpholinyl, imidazolyl, aminothiadiazolyl, pyrrolidinyl, piperazinyl, pyridinyl or piperidinyl ring; or $R^1$ and $R^2$ together with N form a piperidinyl, pyrrolidinyl, piperazinyl, morpholinyl, thiomorpholinyl, imidazolyl, or aminothiadiazolyl ring.

8. The method of claim 1, wherein each R is H or halo.

9. The method of claim 1, wherein one of A and V is H or halo.

10. The method of claim 9, wherein said halo is fluoro or chloro.

11. The method of claim 1, wherein each Z is H, halo, or $SR^2$ wherein $R^2$ is $C_{1-10}$ alkyl.

12. The method of claim 1, wherein each L and L¹ is halo.

13. The method of claim 1, comprising contacting said compound having formula (6A) and said compound having formula (7) to form a mixture, and contacting said mixture with said base.

14. The method of claim 13, wherein said mixture is cooled to a temperature below room temperature, and contacting the base with said mixture.

15. The method of claim 13, wherein said base is contacted with said mixture at room temperature or at a temperature above room temperature.

16. The method of claim 1, wherein said base is an amine.

17. The method of claim 16, wherein said amine is trialkylamine.

18. The method of claim 1, wherein said compound having formula (6A) is contacted with said compound having formula (7) to produce a compound having formula (4)

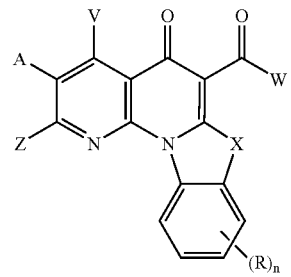
(4)

wherein n, W, and R are as defined in formula (1) in claim 1;
Z is $NR^1R^2$; and
each of V and A is independently H or halo.

19. The method of claim 1, wherein the compound having formula (6A) is contacted with a compound of formula (7) or tautomers thereof in the presence of said non-nucleophilic base and a Lewis acid.

20. The method of claim 19, wherein said non-nucleophilic base is triethylamine, diisopropyl ethyl amine, diazabicycloundecene, cesium carbonate, 1,8-Bis(dimethylamino) naphthalene or dimethylamino pyridine (DMAP).

21. The method of claim 19, wherein said Lewis acid has formula $ML_n$, wherein L is a halogen atom or an organic radical, n is 3-5, and M is a group II metal, group III elemental atom, Zr, Ti, Sn, As, Sb, V or Fe.

22. The method of claim 21, wherein said group III elemental atom is B, or wherein said Lewis acid is $MgCl_2$.

* * * * *